United States Patent
Gohno

(10) Patent No.: US 7,756,243 B2
(45) Date of Patent: Jul. 13, 2010

(54) DOSE EVALUATING METHOD AND X-RAY CT APPARATUS

(75) Inventor: Makoto Gohno, Tokyo (JP)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 11/290,939

(22) Filed: Nov. 30, 2005

(65) Prior Publication Data

US 2006/0115039 A1   Jun. 1, 2006

(30) Foreign Application Priority Data

Dec. 1, 2004   (JP)   ............... 2004-348730

(51) Int. Cl.
*A61B 6/00* (2006.01)

(52) U.S. Cl. ............................ 378/16; 378/4

(58) Field of Classification Search .............. 378/4, 378/19, 108–115
See application file for complete search history.

(56) References Cited

U.S. PATENT DOCUMENTS

| | | | |
|---|---|---|---|
| 4,309,614 A * | 1/1982 | Wagner | 378/16 |
| 5,379,333 A * | 1/1995 | Toth | 378/16 |
| 5,400,378 A * | 3/1995 | Toth | 378/16 |
| 5,450,462 A * | 9/1995 | Toth et al. | 378/16 |
| 5,459,769 A * | 10/1995 | Brown | 378/4 |
| 5,485,494 A * | 1/1996 | Williams et al. | 378/16 |
| 5,696,807 A * | 12/1997 | Hsieh | 378/109 |
| 5,822,393 A * | 10/1998 | Popescu | 378/108 |
| 5,867,555 A * | 2/1999 | Popescu et al. | 378/16 |
| 5,949,811 A * | 9/1999 | Baba et al. | 378/108 |
| 6,115,077 A * | 9/2000 | Tsukagoshi | 348/607 |
| 6,295,336 B1 * | 9/2001 | Aach et al. | 378/108 |
| 6,775,352 B2 * | 8/2004 | Toth et al. | 378/108 |
| 6,901,129 B2 * | 5/2005 | Tachizaki et al. | 378/4 |
| 7,031,423 B2 * | 4/2006 | Tsukagoshi | 378/4 |
| 7,103,139 B2 | 9/2006 | Nagaoka et al. | |

(Continued)

FOREIGN PATENT DOCUMENTS

JP   09-313476   12/1997

(Continued)

OTHER PUBLICATIONS

Makoto Gohno; Patent Application "Radiation Imaging Apparatus"; Filed Nov. 21, 2005; 28 pgs.

(Continued)

*Primary Examiner*—Edward J Glick
*Assistant Examiner*—Alexander H Taningco
(74) *Attorney, Agent, or Firm*—Armstrong Teasdale LLP

(57) ABSTRACT

With the objective of evaluating whether a dose is excessive for a subject, such a dose that image noise reaches less than or equal to a predetermined value is estimated upon an axial scan on the basis of projection data acquired by a scout scan. The dose is set as a maximum dose. An area other than air, of an image obtained by the axial scan is partitioned into a plurality of small areas i. Image noises N(i) at the respective small areas i are calculated. A warning image G1 in which all of pixel values of pixels in small areas in which the image noises N(i) are less than or equal to a predetermined value, are substituted with pixel values expressed in black level, is created and displayed.

8 Claims, 5 Drawing Sheets

U.S. PATENT DOCUMENTS

| | | | |
|---|---|---|---|
| 2003/0016778 A1* | 1/2003 | Tachizaki et al. | 378/4 |
| 2004/0247071 A1* | 12/2004 | Dafni | 378/16 |
| 2005/0094761 A1 | 5/2005 | Hagiwara | |
| 2005/0185759 A1* | 8/2005 | Toth et al. | 378/109 |

FOREIGN PATENT DOCUMENTS

| | | | |
|---|---|---|---|
| JP | 10-308899 | | 11/1998 |
| JP | 2002263097 | | 9/2002 |
| JP | 2002263097 | A * | 9/2002 |
| JP | 2003079611 | | 3/2003 |
| JP | 2003079611 | A * | 3/2003 |
| JP | 2004-065815 | | 3/2004 |

OTHER PUBLICATIONS

Masaru Seto et al.; Patent Application "Scan Program Communication Method and X-Ray CT Apparatus"; U.S. Appl. No. 11/179,872, filed Jul. 12, 2005; 15 pgs.

* cited by examiner

Target Image
G 0

Target Image
G 0 i
Small Area

Warning Image
G 1 i
Small Area q
Pixel-Value
Substituted Portion

DOSE EVALUATING METHOD AND X-RAY CT APPARATUS

CROSS REFERENCE TO RELATED APPLICATIONS

This application claims the benefit of Japanese Application No. 2004-348730 filed Dec. 1, 2004.

This application claims the benefit of Japanese Application No. 2004-348730 filed Dec. 1, 2004, incorporated by reference herein in its entirety.

There has heretofore been known an X-ray apparatus which controls the output of an X-ray tube at the time of real imaging of a subject on the basis of a histogram indicative of pixel values for a preliminary image obtained by preliminarily imaging the subject by the X-ray apparatus (refer to, for example, a patent document 1).

[Patent Document 1] Japanese Patent Publication No. Hei 10(1998)-308899

The conventional X-ray apparatus was capable of preventing a dose at the real imaging from becoming excessive for the subject.

However, there is a need to collect, by preliminary imaging, projection data corresponding to all views, which are necessary to reconstruct the preliminary image, thus causing a problem that the preliminary imaging becomes complex. Also a problem arises in that it is not possible to evaluate whether a dose at the photography of an already reconstructed image is in excess.

SUMMARY OF THE INVENTION

Therefore, an object of the present invention is to provide a dose evaluating method capable of estimating a dose excessive for a subject even though projection data corresponding to all views, which are necessary for image reconstruction, are not collected, a dose evaluating method capable of evaluating whether a dose at the photography of an already reconstructed image is excessive, and an X-ray CT apparatus capable of suitably implementing those methods.

In a first aspect, the present invention provides a dose evaluating method comprising the steps of collecting projection data (called fixed view projection data) without rotating an X-ray tube and an X-ray detector about a body axis of a subject, and evaluating, based on the fixed view projection data, a dose at the time when at least one of the X-ray tube and the X-ray detector is rotated about the body axis of the subject to collect projection data.

In the dose evaluating method according to the first aspect, there is no need to collect projection data corresponding to all views necessary for image reconstruction because the dose is evaluated based on the fixed view projection data.

In a second aspect, the present invention provides a dose evaluating method wherein in the dose evaluating method according to the first aspect, an average transmission density and a maximum transmission length are determined from the fixed view projection data, a dose at which image noise reaches less than or equal to a predetermined value is estimated from the average transmission density and the maximum transmission length, and the dose is set as a criterion for evaluation.

In the dose evaluating method according to the second aspect, an average transmission density and a maximum transmission length inherent in a subject are extracted from fixed view projection data. Next, such a dose that image noise becomes a predetermined value (determined according to a region to be imaged and imaging purposes) or less with respect to the average transmission density and the maximum transmission length inherent in the subject, is estimated. Then, whether the dose is excessive with the estimated dose as a criterion for evaluation, is estimated.

Incidentally, the image noise can be utilized with, for example, a dispersion value of pixel values as an index.

In a third aspect, the present invention provides a dose evaluating method wherein in the dose evaluating method according to the second aspect, the dose set as the criterion for evaluation is exhibited as a maximum dose when an operator designates a dose at the time when at least one of the X-ray tube and the X-ray detector is rotated about the body axis of the subject to collect the projection data.

In the dose evaluating method according to the third aspect, the operator has designated the dose less than or equal to the exhibited maximum dose. Thus, the dose can be prevented from becoming excessive for the subject.

In a fourth aspect, the present invention provides a dose evaluating method comprising the steps of collecting projection data (called fixed view projection data) at a plurality of z-coordinate positions without rotating an X-ray tube and an X-ray detector about a body axis of a subject and by moving the X-ray tube and the X-ray detector relative to the direction of the body axis thereof, and evaluating, based on the fixed view projection data, doses at the respective z-coordinate positions at the time when at least one of the X-ray tube and the X-ray detector is rotated about the body axis of the subject to collect projection data.

In the dose evaluating method according to the fourth aspect, the doses at the plurality of z-coordinate positions are evaluated based on the fixed view projection data obtained by a scout scan. It is therefore unnecessary to collect projection data corresponding to all views necessary for image reconstruction at the plural z-coordinate positions.

In a fifth aspect, the present invention provides a dose evaluating method wherein in the dose evaluating method according to the fourth aspect, average transmission densities and maximum transmission lengths at the respective z-coordinate positions are determined from the respective fixed view projection data, doses at which image noises at the respective z-coordinate positions become less than or equal to a predetermined value, are estimated from the respective average transmission densities and the maximum transmission lengths, and the respective doses are set as criteria for evaluation at the respective z-coordinate positions.

In the dose evaluating method according to the fifth aspect, the average transmission densities and the maximum transmission lengths inherent in the subject at the plurality of z-coordinate positions are extracted from the fixed view projection data at the respective z-coordinate positions. Next, such doses that image noises become a predetermined value (determined according to a region to be imaged and imaging purposes) or less with respect to the average transmission densities and the maximum transmission lengths inherent in the subject at the z-coordinate positions, are estimated. Then, whether the doses at the respective z-coordinate positions are excessive with these estimated doses as criteria for evaluation, is estimated.

Incidentally, the image noise can be utilized with, for example, a dispersion value of pixel values in respective small areas as indices.

In a sixth aspect, the present invention provides a dose evaluating method wherein in the dose evaluating method according to the fifth aspect, a dose set as a criterion for evaluation at a given z-coordinate position is exhibited as a maximum dose when an operator designates a dose at the time when at least one of the X-ray tube and the X-ray detector is rotated about the body axis of the subject to collect projection data.

In the dose evaluating method according to the sixth aspect, the operator has designated the dose less than or equal to the exhibited maximum dose. Thus, it is possible to prevent the dose from becoming excessive for the subject.

In a seventh aspect, the present invention provides a dose evaluating method comprising the steps of partitioning an area for a target image, other than air into a plurality of small areas, calculating image noise at each of the small areas, and if a small area in which the image noise is less than or equal to a predetermined value exists, determining as being excessive, a dose at the time when the target image is photographed.

In the dose evaluating method according to the seventh aspect, whether a dose at the photography of an already reconstructed image is excessive, can be evaluated.

Incidentally, the image noise can be utilized with, for example, a dispersion value of pixel values in respective small areas as indices.

In an eighth aspect, the present invention provides a dose evaluating method wherein in the dose evaluating method according to the seventh aspect, a display form of the small area at the time when the dose is determined as being excessive, is changed to create and display a warning image which enables a distinction from each small area in which image noise is larger than a predetermined value.

In the dose evaluating method according to the eighth aspect, a warning image in which only the small area at the time when the dose is determined as being excessive, is represented in blink, for example, is created and displayed. It is therefore possible to exhibit to an operator, whether the dose at the photography of a target image is excessive.

In a ninth aspect, the present invention provides a dose evaluating method wherein in the dose evaluating method according to the seventh or eighth aspect, a histogram in which the value of image noise is defined as a horizontal axis and the number of small areas is defined as a vertical axis, is created and displayed.

In the dose evaluating method according to the ninth aspect, the operator is able to visually recognize the ratio between each small area in which the dose is determined as being excessive and the whole region to be imaged.

In a tenth aspect, the present invention provides an X-ray CT apparatus comprising fixed view projection data acquiring means for collecting projection data (called fixed view projection data) without rotating an X-ray tube and an X-ray detector about a body axis of a subject, and dose evaluating means for evaluating, based on the fixed view projection data, a dose at the time when at least one of the X-ray tube and the X-ray detector is rotated about the body axis of the subject to collect projection data.

The X-ray CT apparatus according to the tenth aspect is capable of suitably implementing the dose evaluating method according to the first aspect.

In an eleventh aspect, the present invention provides an X-ray CT apparatus wherein in the X-ray CT apparatus according to the tenth aspect, the dose evaluating means determines an average transmission density and a maximum transmission length from the fixed view projection data, estimates a dose at which image noise reaches less than or equal to a predetermined value, from the average transmission density and the maximum transmission length, and sets the dose as a criterion for evaluation.

The X-ray CT apparatus according to the eleventh aspect is capable of suitably implementing the dose evaluating method according to the second aspect.

In a twelfth aspect, the present invention provides an X-ray CT apparatus wherein in the X-ray CT apparatus according to the eleventh aspect, dose designating means for allowing an operator to designate a dose at the time when at least one of the X-ray tube and the X-ray detector is rotated about the body axis of the subject to collect projection data, and maximum dose exhibiting means for exhibiting the dose set as the criterion for evaluation as a maximum dose are provided.

The X-ray CT apparatus according to the twelfth aspect is capable of suitably implementing the dose evaluating method according to the third aspect.

In a thirteenth aspect, the present invention provides an X-ray CT apparatus comprising fixed view projection data acquiring means for collecting projection data (called fixed view projection data) at a plurality of z-coordinate positions without rotating an X-ray tube and an X-ray detector about a body axis of a subject and by moving the X-ray tube and the X-ray detector relative to the direction of the body axis thereof, and dose evaluating means for evaluating, based on the fixed view projection data, doses at the respective z-coordinate positions at the time when at least one of the X-ray tube and the X-ray detector is rotated about the body axis of the subject to collect projection data.

The X-ray CT apparatus according to the thirteenth aspect is capable of suitably implementing the dose evaluating method according to the fourth aspect.

In a fourteenth aspect, the present invention provides an X-ray CT apparatus wherein in the X-ray CT apparatus according to the thirteenth aspect, the dose evaluating means determines average transmission densities and maximum transmission lengths at the respective z-coordinate positions from the respective fixed view projection data, estimates doses at which image noises at the respective z-coordinate positions become less than or equal to a predetermined value, from the respective average transmission densities and the maximum transmission lengths, and sets the respective doses as criteria for evaluation at the respective z-coordinate positions.

The X-ray CT apparatus according to the fourteenth aspect is capable of suitably implementing the dose evaluating method according to the fifth aspect.

In a fifteenth aspect, the present invention provides an X-ray CT apparatus wherein in the X-ray CT apparatus according to the fourteenth aspect, dose designating means for allowing an operator to designate a dose at the time when at least one of the X-ray tube and the X-ray detector is rotated about the body axis of the subject at a given z-coordinate position to collect projection data, and maximum dose exhibiting means for exhibiting a dose set as a criterion for evaluation at the given z-coordinate position as a maximum dose are provided.

The X-ray CT apparatus according to the fifteenth aspect is capable of suitably implementing the dose evaluating method according to the sixth aspect.

In a sixteenth aspect, the present invention provides an X-ray CT apparatus comprising image noise calculating means for partitioning an area for a target image, other than air into a plurality of small areas and calculating image noise at each small area, and dose evaluating means for, if a small area in which the image noise is less than or equal to a predetermined value exists, determining as being excessive, a dose at the time when the target image is photographed.

The X-ray CT apparatus according to the sixteenth aspect is capable of suitably implementing the dose evaluating method according to the seventh aspect.

In a seventeenth aspect, the present invention provides an X-ray CT apparatus wherein in the X-ray CT apparatus according to the sixteenth aspect, warning image creating/ displaying means for creating and displaying a warning image which enables a distinction from each small area in which image noise is larger than a predetermined value, by changing a display form of the small area at the time when the dose is determined as being excessive.

The X-ray CT apparatus according to the seventeenth aspect is capable of suitably implementing the dose evaluating method according to the eighth aspect.

In an eighteenth aspect, the present invention provides an X-ray CT apparatus wherein in the X-ray CT apparatus according to the sixteenth or seventeenth aspect, histogram creating/displaying means for creating and displaying a histogram in which the value of image noise is defined as a horizontal axis and the number of small areas is defined as a vertical axis, is provided.

The X-ray CT apparatus according to the eighteenth aspect is capable of suitably implementing the dose evaluating method according to the ninth aspect.

According to a dose evaluating method and an X-ray CT apparatus of the present invention, it is possible to estimate a dose excessive for a subject even though projection data corresponding to all views necessary for image reconstruction are not collected. It is also possible to evaluate whether a dose at the time when an already-reconstructed image is photographed, is in excess.

The dose evaluating method and the X-ray CT imaging method according to the present invention can be used for evaluating whether a dose is excessive for each subject.

Further objects and advantages of the present invention will be apparent from the following description of the preferred embodiments of the invention as illustrated in the accompanying drawings.

DETAILED DESCRIPTION OF THE INVENTION

Figure 1:
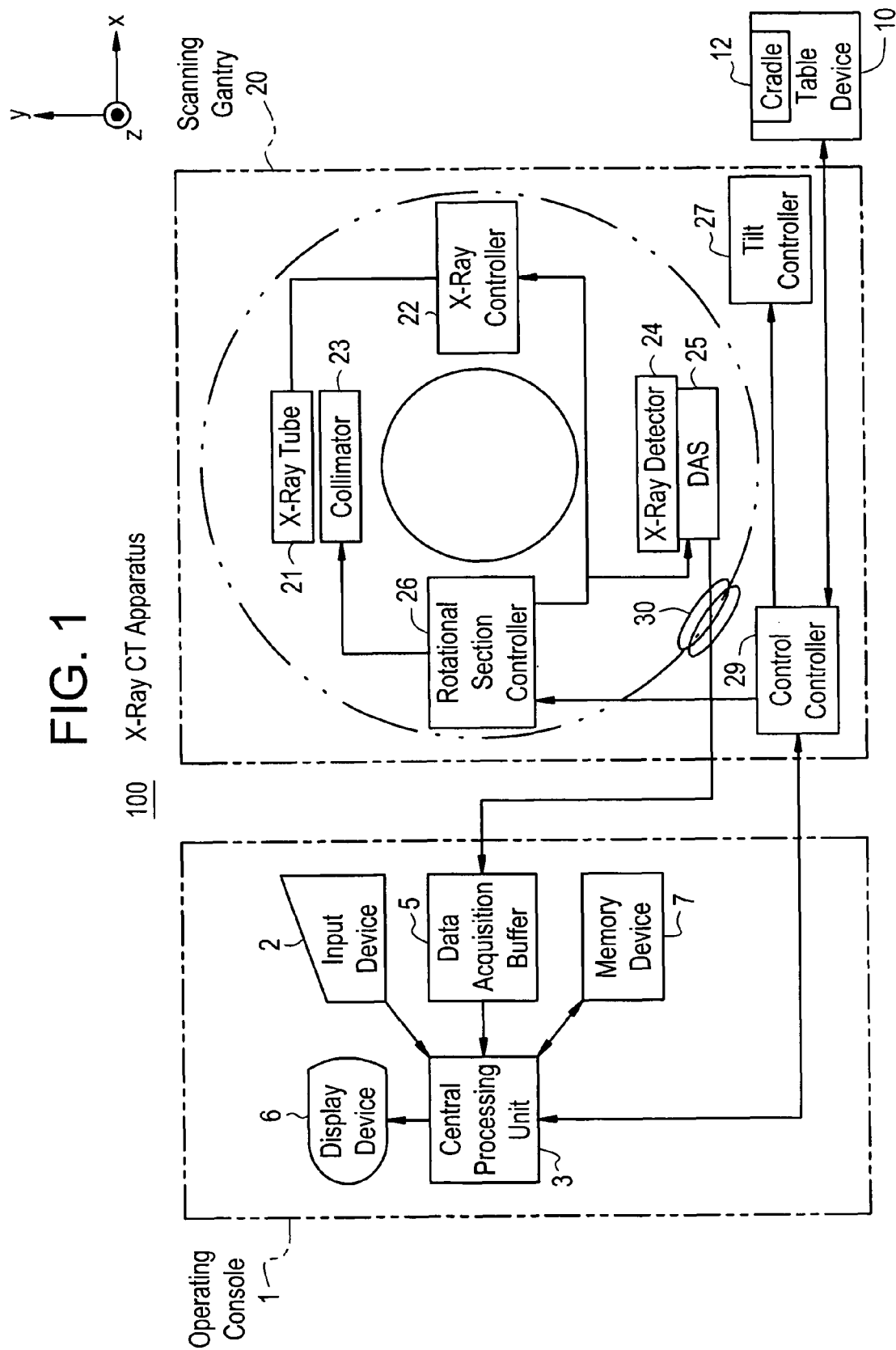
FIG. 1 is a block diagram showing an X-ray CT apparatus according to an embodiment 1.

The present invention will hereinafter be described in further detail according to embodiments illustrated in the drawings. Incidentally, the present invention is not limited thereby.

Embodiment 1

FIG. 1 is a schematic block diagram showing an X-ray CT apparatus according to an embodiment 1.

The X-ray CT apparatus 100 is equipped with an operating console 1, a table device 10 and a scanning gantry 20.

The operating console 1 is provided with an input device 2 which receives an operator's input, a central processing unit 3 which executes various processes, a data acquisition buffer 5 which collects projection data obtained by the scanning gantry 20, a display device 6 which displays a CT image or the like image-reconstructed from the projection data, and a memory device 7 which stores programs, data and an image therein.

The table device 10 includes a cradle 12 which places a subject thereon and inserts and draws it into and from a bore (cavity section). The cradle 12 is elevated and linearly moved by a motor built in the table device 10.

The scanning gantry 20 is provided with an X-ray tube 21, an X-ray controller 22, a collimator 23, an X-ray detector 24, a DAS (Data Acquisition System) 25, a rotational section controller 26 which controls the X-ray tube 21 rotated about a body axis of the subject, etc., a tilt controller 27 which performs control of the scanning gantry 20 at the time when the scanning gantry 20 is tilted forward or backward of its rotational axis, a control controller 29 which performs a transfer of a control signal or the like between the operating console 1 and the table device 10, and a slip ring 30 which transfers a power supply, a control signal and collected projection data.

Figure 2:
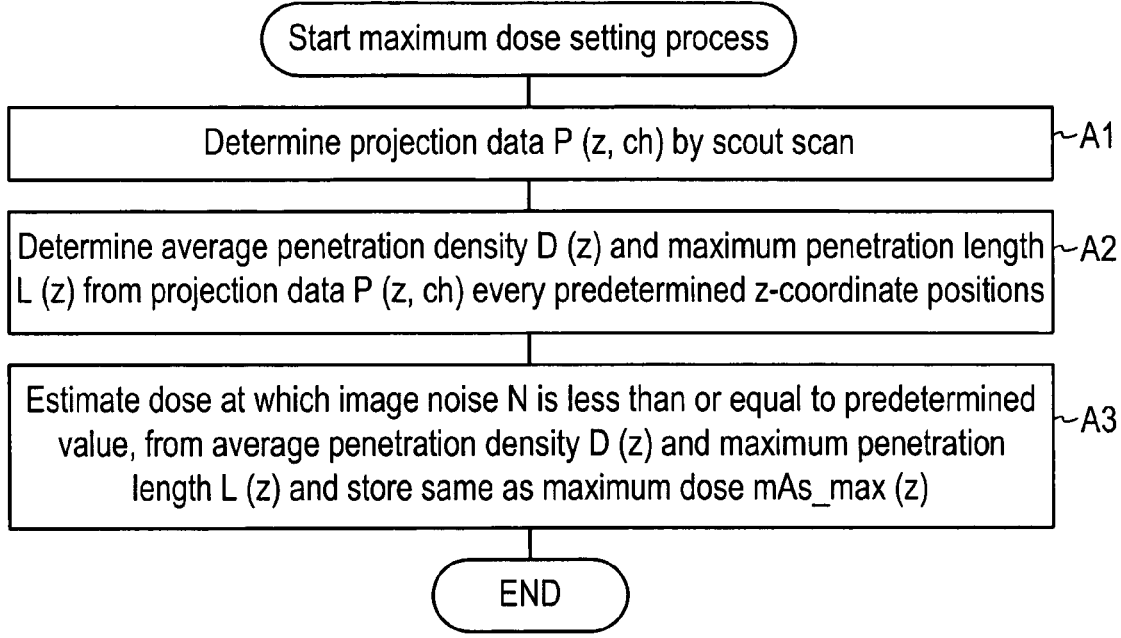
FIG. 2 is a flowchart depicting a procedure for performing a maximum dose setting process.

FIG. 2 is a flowchart showing a procedure for performing a maximum dose setting process by the X-ray CT apparatus 100.

Figure 3:
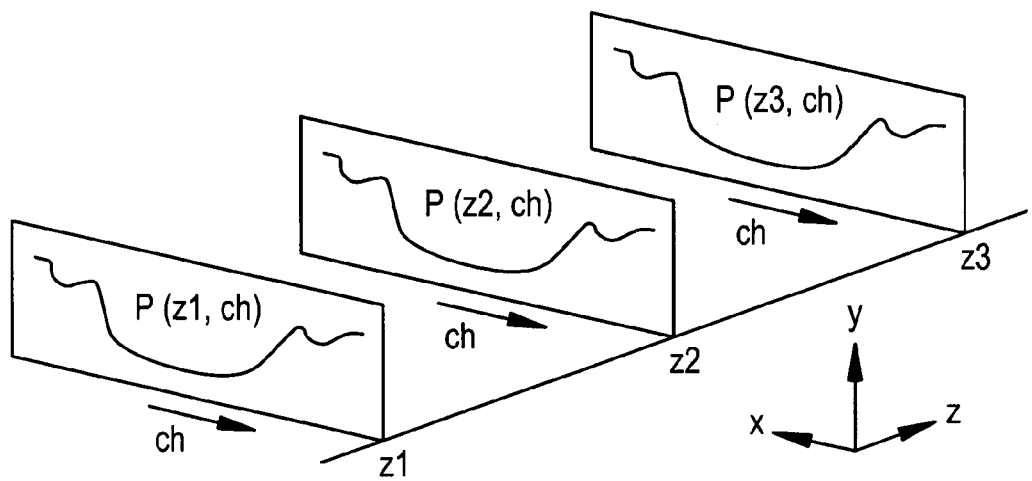
FIG. 3 is a conceptual diagram showing projection data P at plurality z-coordinate positions.

At Step A1, the subject is scout-scanned to collect or acquire projection data P (z, ch). FIG. 3 conceptually shows projection data P (z, ch) at a plurality of z coordinate positions.

At Step A2, an average transmission density D (z) and a maximum transmission length L (z) are determined from the projection data P (z, ch) every predetermined z coordinate positions.

At Step A3, such a dose that image noise is less than or equal to a predetermined value with respect to the average transmission density D (z) and the maximum transmission length L (z), is estimated and stored as a maximum dose mAs_max(z). This estimation makes it possible to determine such a dose that the image noise becomes less than or equal to the predetermined value with respect to the average transmission density D (z) and the maximum transmission length L (z) by reference to data about an average transmission density, a maximum transmission length, doses and image noise, which have been created by, for example, actual measurement or simulation in advance. Alternatively, the maximum dose can be calculated from the following equation using such functions f and g that the image noise becomes a predetermined value, which functions have been determined by actual measurement or simulation in advance.

$$mAs\_max(z) = max\{f(D(z)), g(L(z))\}$$

where max {,} indicates a function which takes a maximum value. f (D(z)) indicates a function which determines such a necessary dose that the image noise reaches the predetermined value, from the average transmission density D (z). g(L(z)) indicates a function which determines such a necessary dose that the image noise becomes the predetermined value, from the maximum transmission length L (z).

Incidentally, the image noise can be utilized with a dispersion value as an index, for example.

Figure 4:
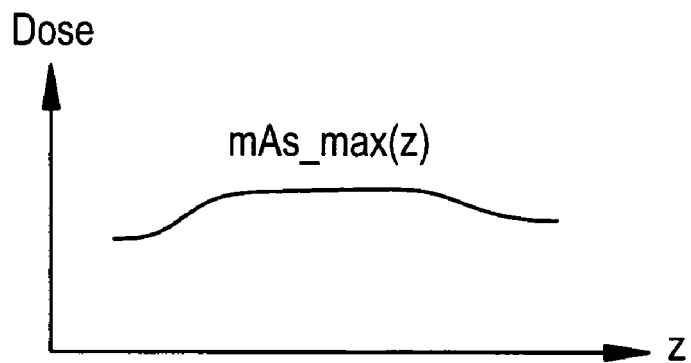
FIG. 4 is an explanatory diagram depicting a relationship between z-coordinate positions and a maximum dose.

The maximum dose mAs_max(z) is conceptually shown in FIG. 4.

Figure 5:
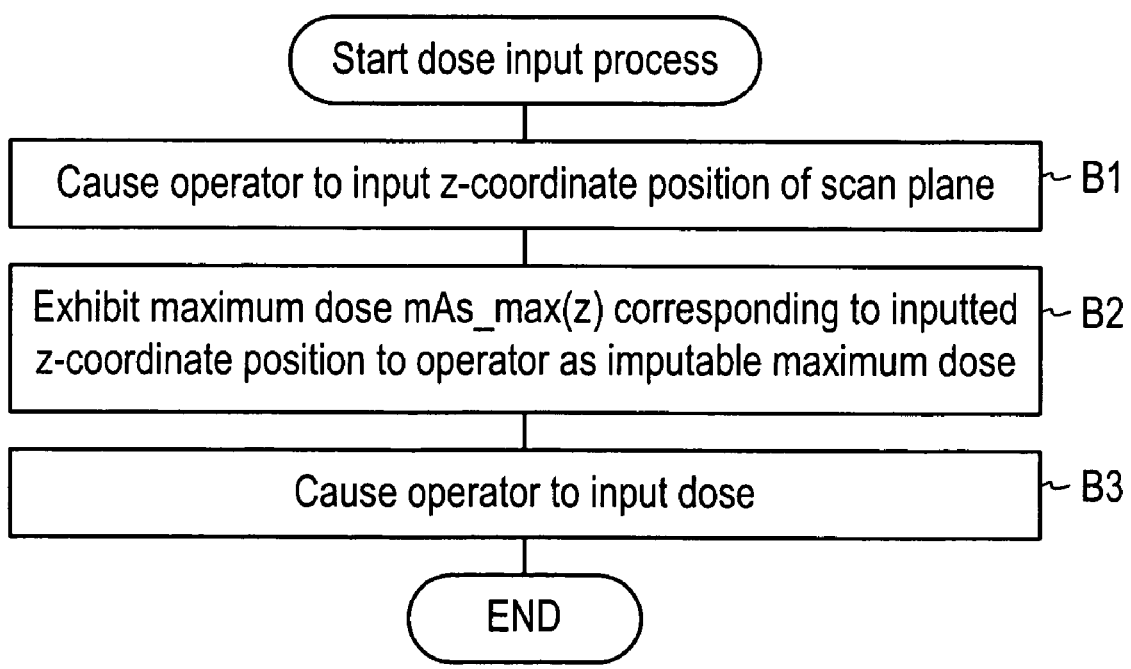
FIG. 5 is a flowchart showing a procedure for performing a dose input process.

FIG. 5 is a flowchart showing a procedure for performing a dose input process by the X-ray CT apparatus 100.

At Step B1, an operator is caused to input each z-coordinate position of a scan plane.

At Step B2, a maximum dose mAs_max(z) corresponding to the inputted z-coordinate position is exhibited to the operator as an inputtable maximum dose.

At Step B3, the operator is caused to input a dose used upon an axial scan. If the operator inputs a dose smaller than the maximum dose exhibited to the operator, then the dose can be prevented from becoming excessive. Incidentally, the operator is also able to dare to input a dose greater than the exhibited maximum dose.

Figure 6:
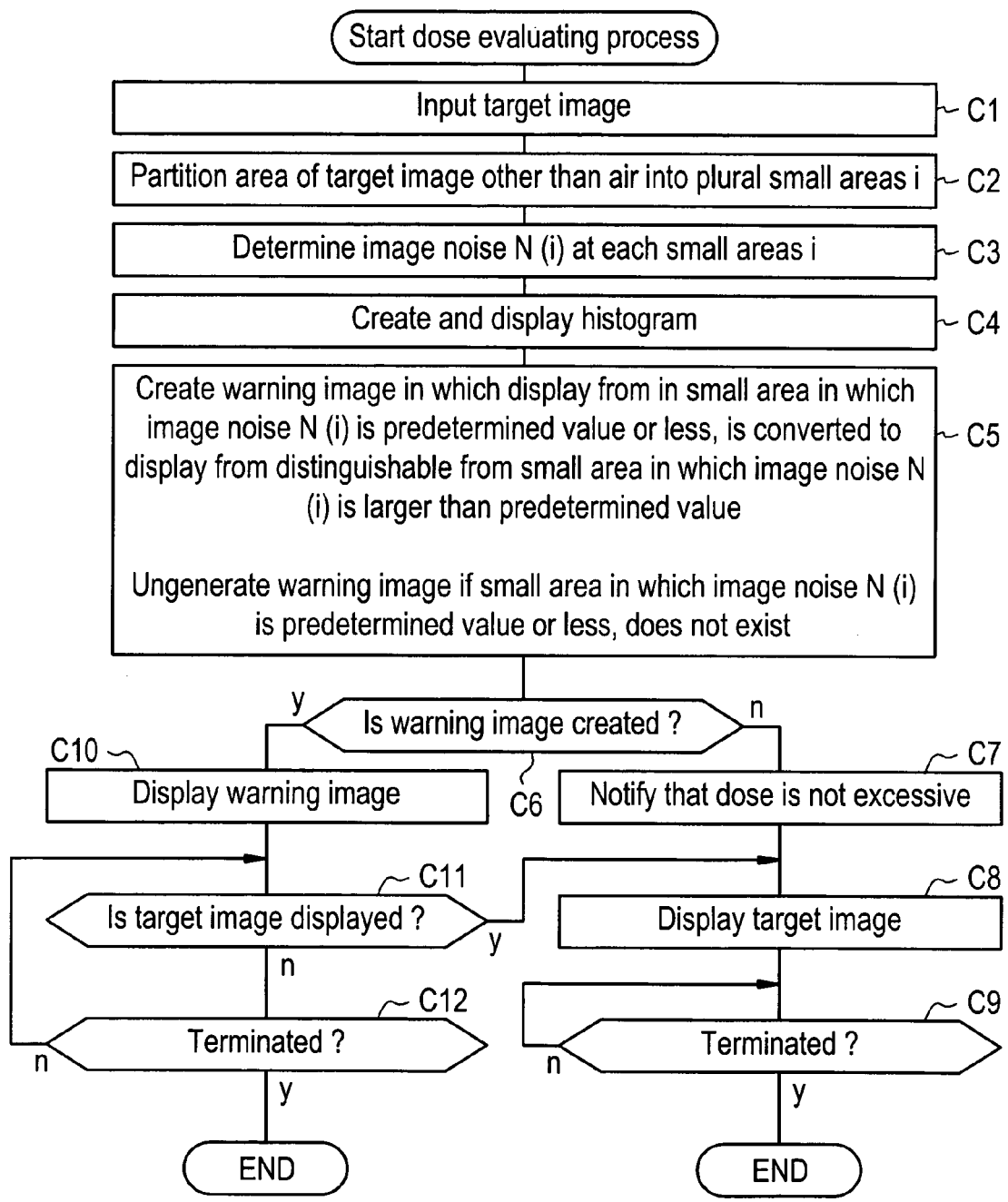
FIG. 6 is a flowchart showing a procedure for performing a dose evaluating process.

FIG. 6 is a flowchart showing a procedure for performing a dose evaluating process by the X-ray CT apparatus 100.

Figure 7:
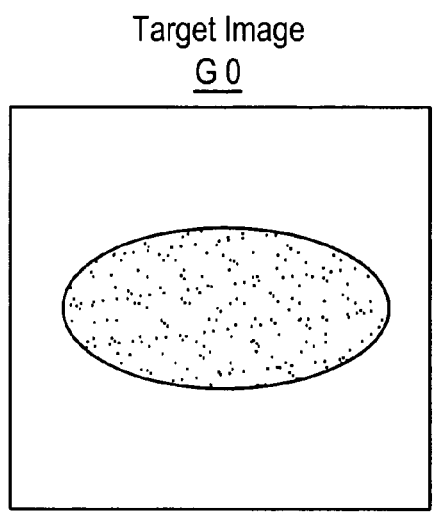
FIG. 7 is a conceptual diagram depicting a target image.

At Step C1, a target image (CT image intended for evaluation) is inputted. Although the target image may be an CT image imaged or photographed by the X-ray CT apparatus 100, it may be an CT image photographed by another X-ray CT apparatus. A target image G0 is conceptually shown in FIG. 7.

Figure 8:
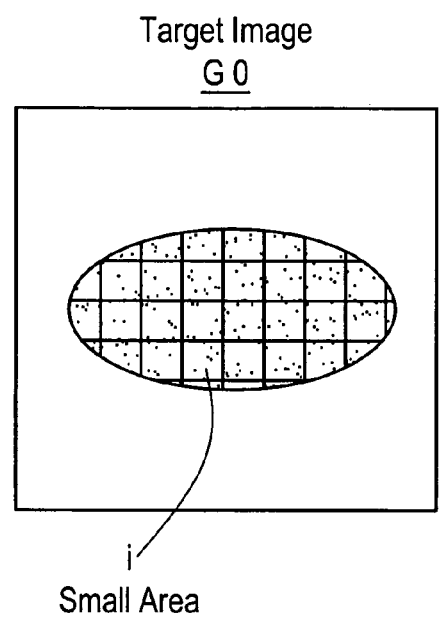
FIG. 8 is a conceptual diagram showing a target image partitioned into small areas.

At Step C2, the area for the target image, other than air is partitioned into a plurality of small areas i as shown in FIG. 8.

At Step C3, image nose N(i) at each small area i is determined. Incidentally, the image noise N(i) can be utilized with, for example, a dispersion value of pixel values at each small area i as an index.

Figure 9:
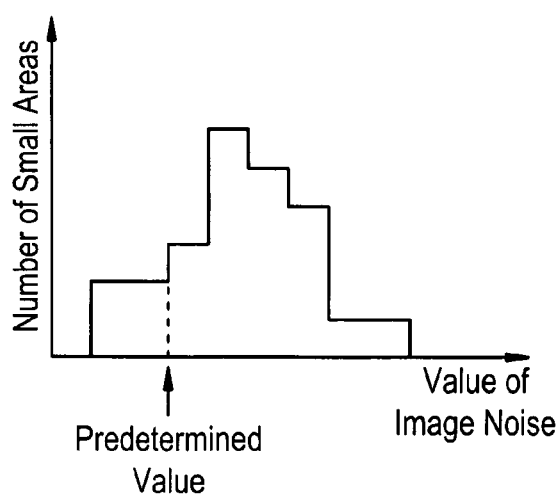
FIG. 9 is a conceptual diagram illustrating a histogram.

At Step C4, a histogram with the value of image noise as the horizontal axis and the number of small areas as the vertical axis is created and displayed as shown in FIG. 9.

At Step C5, a warning image is created wherein a display form of each small area in which the image noise N(i) is less than or equal to a predetermined value, is converted into a display form distinguishable from each small area in which the image noise N(i) is larger than the predetermined value. For example, all pixel values of pixels in each small area in which the image noise N(i) is less than or equal to the predetermined value, are substituted with pixel values each expressed in black level. Alternatively, a specific color like an orange color is overlaid on each small area in which the image noise N(i) is less than or equal to the predetermined value. Alternatively, the pixel values of the pixels in each small area in which the image nose N(i) is less than or equal to the predetermined value, are converted into pixel values represented in blink or highlight.

Figure 10:
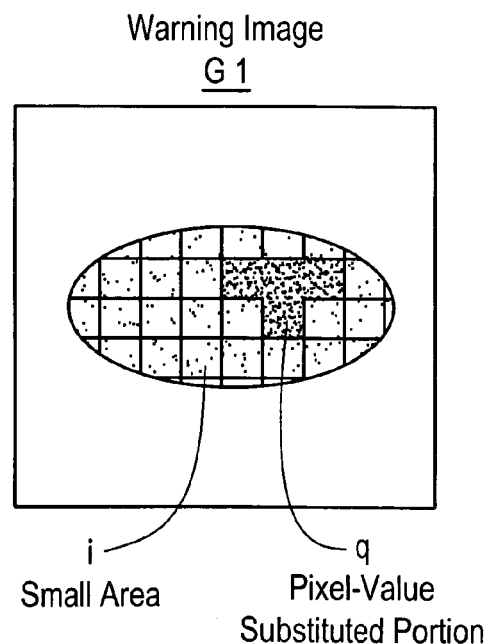
FIG. 10 is a conceptual diagram showing a warning image.

A warning image G1 is conceptually shown in FIG. 10.

Incidentally, no warning image is created if each small area in which the image noise N(i) is less than or equal to the predetermined value, does not exist.

At Step C6, the procedure proceeds to Step C7 if no warning image G1 is created. If it has been created, then the procedure proceeds to Step C10.

At Step C7, the X-ray CT apparatus 100 notifies that the dose is not in excess.

At Step C8, the original target image G0 is displayed.

At Step C9, the dose evaluating process is placed in a waiting state until the operator issues an instruction for "end". If the instruction for "end" is issued, then the dose evaluating process is terminated.

At Step C10, the warning image G1 is displayed.

At Step C11, the procedure proceeds to Step C8 if the operator has issued an instruction for "display of target image". If not so, then the procedure proceeds to Step C12.

At Step C12, the dose evaluating process is terminated if the operator issues the instruction for "end". If not so, then the procedure is returned to Step C11.

Embodiment 2

If the minimum value of the maximum dose mAs_max(z) at a linearly-moved range (range at each z-coordinate position) is assumed to be of a maximum dose where a helical scan is performed under a constant dose, then no dose is made excessive even at any point of the linearly-moved range. On the other hand, if the maximum value of the maximum dose mAs_max(z) at the linearly-moved range is assumed to be of a maximum dose, then image noise reaches less than equal to a predetermined value even at any point of the linearly-moved range.

Many widely different embodiments of the invention may be configured without departing from the spirit and the scope of the present invention. It should be understood that the present invention is not limited to the specific embodiments described in the specification, except as defined in the appended claims.

The invention claimed is:

1. A dose evaluating method comprising:
   collecting fixed view projection data using a scout scan performed without rotating an X-ray tube and an X-ray detector about a body axis of a subject;
   estimating a dose for use in a scan performed by rotating at least one of the X-ray tube and the X-ray detector about the body axis of the subject, the dose estimated based on the fixed view projection data and based on at least one of a region of the subject imaged during the scan and an imaging purpose of the scan;
   displaying the estimated dose as a maximum dose before the scan;
   selecting a single constant dose value to be used during the scan based on the maximum dose;
   performing the scan using the single constant dose value throughout the scan to produce projection data; and
   generating an image based on the projection data, the image having image noise one of less than a predetermined value and equal to the predetermined value.

2. A dose evaluating method comprising:
   collecting fixed view projection data at a plurality of z-coordinate positions using a scout scan performed without rotating an X-ray tube and an X-ray detector about a body axis of a subject, the scout scan performed by moving the X-ray tube and the X-ray detector relative to the direction of the body axis of the subject;
   estimating a dose for use in a scan performed by rotating at least one of the X-ray tube and the X-ray detector about the body axis of the subject, the dose estimated based on the fixed view projection data and based on at least one of a region of the subject imaged during the scan and an imaging purpose of the scan;
   displaying the estimated dose as a maximum dose before the scan;
   selecting a single constant dose value to be used throughout the scan based on the maximum dose;
   performing the scan using the single constant dose value throughout the scan to produce projection data; and
   generating an image based on the projection data, the image having image noise one of less than a predetermined value and equal to the predetermined value.

3. A dose evaluating method comprising:
   partitioning an area for a target image, other than air, into a plurality of small areas, the target image generated based on projection data acquired during a scan performed by rotating an X-ray tube and an X-ray detector about a body axis of a subject;
   calculating image noise at each of the small areas;

creating a warning image which enables a distinction from each small area in which image noise is greater than a predetermined value, by changing a display form of the small area; and displaying the warning image to indicate an excessive dose when the target image is photographed.

4. The dose evaluating method according to claim 3, further comprising creating and displaying a histogram in which the value of image noise is defined as a horizontal axis and the number of small areas is defined as a vertical axis.

5. An X-ray CT apparatus comprising:
a projection data acquiring device configured to:
collect fixed view projection data generated during a scout scan performed without rotating an X-ray tube and an X-ray detector about a body axis of a subject; and
collect projection data generated during a scan performed by rotating the X-ray tube and the X-ray detector about the body axis of the subject, the projection data collected at a single constant dose value throughout the scan;
a dose estimating device configured to estimate a dose for use during the scan in order to generate an image based on the projection data, the image having image noise one of less than a predetermined value and equal to the predetermined value, the dose estimated based on the fixed view projection data and based on at least one of a region of the subject imaged during the scan and an imaging purpose of the scan;
a display device configured to display to an operator the estimated dose as a maximum dose before the scan; and
a designating device configured to receive a single constant dose value selection from the operator for use throughout the scan, the single constant dose value selection based on the maximum dose.

6. An X-ray CT apparatus comprising:
a projection data acquiring device configured to:
collect fixed view projection data at a plurality of z-coordinate positions generated during a scout scan performed without rotating an X-ray tube and an X-ray detector about a body axis of a subject, the scout scan performed by moving the X-ray tube and the X-ray detector relative to the direction of the body axis of the subject; and
collect projection data generated during a scan performed by rotating the X-ray tube and the X-ray detector about the body axis of the subject, the projection data collected at a single constant dose value throughout the scan;
a dose estimating device configured to estimate a dose for use during the scan in order to generate an image based on the projection data, the image having image noise one of less than a predetermined value and equal to the predetermined value, the dose estimated based on the fixed view projection data and based on at least one of a region of the subject imaged during the scan and an imaging purpose of the scan;
a display device configured to display to an operator the estimated dose as a maximum dose before the scan; and
a designating device configured to receive a single constant dose value selection from the operator for use throughout the scan, the single constant dose value selection based on the maximum dose.

7. An X-ray CT apparatus comprising:
an image noise calculating device configured to partition an area for a target image, other than air, into a plurality of small areas and to calculate image noise at each small area, the target image generated based on projection data acquired during a scan performed by rotating an X-ray tube and an X-ray detector about a body axis of a subject; and
a dose evaluating device configured to create a warning image which enables a distinction from each small area in which image noise is greater than a predetermined value, by changing a display form of the small area and to display the warning image to indicate an excessive dose when the target image is photographed.

8. The X-ray CT apparatus according to claim 7, further comprising:
a histogram creating/displaying device configured to create a histogram in which the value of image noise is defined as a horizontal axis and the number of small areas is defined as a vertical axis, and to display the histogram.

* * * * *